(12) United States Patent
Huber

(10) Patent No.: US 6,313,157 B1
(45) Date of Patent: Nov. 6, 2001

(54) INSECTICIDAL METHOD

(75) Inventor: Scot Kevin Huber, Raleigh, NC (US)

(73) Assignee: Rhone-Poulenc Agro, Lyons (FR)

( * ) Notice: Subject to any disclaimer, the term of this patent is extended or adjusted under 35 U.S.C. 154(b) by 0 days.

(21) Appl. No.: 09/352,358

(22) Filed: Jul. 13, 1999

(30) Foreign Application Priority Data

Jun. 4, 1999 (EP) .................................................. 99110709

(51) Int. Cl.$^7$ .................................................... A01N 43/56
(52) U.S. Cl. ........................... 514/407; 514/404; 514/406
(58) Field of Search ...................................... 514/404, 406, 514/407

(56) References Cited

U.S. PATENT DOCUMENTS

| | | | | |
|---|---|---|---|---|
| 5,885,607 | * | 3/1999 | Jeannin | 424/411 |
| 6,096,329 | * | 8/2000 | Jeannin | 424/405 |

* cited by examiner

Primary Examiner—Allen J. Robinson
(74) Attorney, Agent, or Firm—Burns, Doane, Swecker & Mathis, L.L.P.

(57) ABSTRACT

A method of control of fleas by applying a 1-arylpyrazole of formula (1) to a locus where the fleas are located or expected to be located.

4 Claims, No Drawings

INSECTICIDAL METHOD

This application claims priority under 35 U.S.C. §119 of Application No. 99 1107095, filed in the European Patent Office on Jun. 4, 1999, incorporated by reference herein.

The present invention relates to a new insecticidal method.

It is well-known to kill insects by means of pyrazole derivatives with insecticidal properties, see inter alia European Patent Publication EP 0295117 and U.S. Pat. No. 5,232,940.

It has also been disclosed to use $SF_5$-phenylpyrazoles against insects connected with public health and resistant to lindane or dieldrin. See International Patent Publications WO 93/06089 and WO 94/21606.

An object of the present invention is to provide a new method of control of fleas which is highly effective.

Another object of the present invention is to provide a method of cleaning animals or animal hair or skin which are or might be infested by fleas.

Another object of the present invention is to provide a method of control of fleas which are not resistant to the insecticides lindane or dieldrin.

These objects are met in whole or in part by the present invention.

The present invention provides a method of control of fleas by applying a 1-arylpyrazole of formula (I) to a locus where the fleas are located or expected to be located, the 1-arylpyrazole being a compound of the formula:

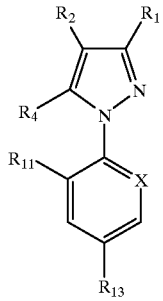

(I)

wherein:
- $R_1$ is CN or methyl;
- $R_2$ is $S(O)_n R_3$,
- $R_3$ is alkyl or haloalkyl;
- $R_4$ is selected from the group comprising a hydrogen atom, a halogen atom, and a radical which may be —$NR_5R_6$, —$C(O)R_7$, —$C(O)OR_7$, —$S(O)_m R_7$, alkyl, haloalkyl, —$OR_8$, or —$N═C(R_9)(R_{10})$;
- $R_5$ and $R_6$ are independently selected from a hydrogen atom, alkyl, haloalkyl, —$C(O)R_7$, —$C(O)OR_7$, —$S(O)_r CF_3$;
- $R_7$ is selected from alkyl or haloalkyl;
- $R_8$ is selected from alkyl, haloalkyl or the hydrogen atom;
- $R_9$ is selected from the hydrogen atom and alkyl;
- $R_{10}$ selected from phenyl or heteroaryl that is optionally substituted by one or more hydroxy, a halogen atom, —O—alkyl, —S-alkyl, cyano, or alkyl or combinations thereof;
- X is selected from the nitrogen atom and the radical C—$R_{12}$;
- $R_{11}$ and $R_{12}$ are independently selected from a halogen atom or the hydrogen atom;
- $R_{13}$ is —$SF_5$;
- m, n, and r are independently selected from 0, 1, and 2.

The alkyl and alkoxy groups of the formula (I) are preferably lower alkyl and alkoxy groups, that is, radicals having one to four carbon atoms. The haloalkyl and haloalkoxy groups likewise preferably have one to four carbon atoms. The haloalkyl and haloalkoxy groups can bear one or more halogen atoms; preferred groups of this type include —$CF_3$ and —$OCF_3$.

A preferred group of 1-arylpyrazoles for use in the present invention are those of formula (1) having one or more of the following features wherein:
- $R_1$ is CN;
- $R_4$ is —$NR_5R_6$;
- $R_5$ and $R_6$ are independently selected from the hydrogen atom, alkyl, haloalkyl, —$C(O)R_7$, —$C(O)OR_7$; or
- X is C—$R_{12}$.

A particularly preferred group of 1-arylpyrazoles for use in the present invention is that wherein:
- $R_1$ is CN;
- $R_4$ is —$NR_5R_6$;
- $R_5$ and $R_6$ are independently selected from the hydrogen atom, alkyl, haloalkyl, —$C(O)R_7$, —$C(O)OR_7$; and
- X is C—$R_{12}$.

It is preferred that $R_4$ is amino.

Specific 1-arylpyrazoles which are preferred include 5-amino-3-cyano-1-(2,6-dichloro-4-pentafluorosulfenylphenyl)-4-trifluoromethysulfinylpyrazole, herein referred to as Compound A; 5-amino-3-cyano-1-(2,6-dichloro-4-pentafluorosulfenylphenyl)-4-trifluoromethylsulfenylpyrazole, herein referred to as Compound B; and 5-amino-3-cyano-1-(2,6-dichloro-4-pentafluorosulfenylphenyl)-4-trifluoromethylsulfonylpyrazole, herein referred to as Compound C.

The locus is preferably a dog or a cat, or the hair or the skin thereof. The arylpyrazole is preferably administered by dermal application, by injection or by oral administration of a bolus or a pill. Dermal administration is preferred, more preferably the so-called spot-on method whereby a small amount of liquid formulation is applied; the application being advantageously made such that the animal cannot reach the place of application with its limbs or tongue, the place being preferably the area between its forward legs and on its back between the shoulder blades.

The dose of the arylpyrazole is from 0.15 mg to 30 mg per kg of body weight of the treated animal, preferably from 0.6 to 15 mg/kg, most preferably from 1.2 to 10 mg/kg.

Compositions for oral administration comprise the active ingredient in association with pharmaceutically acceptable carriers or coatings and include, for example, tablets, pills, capsules, gels, drenches, medicated feeds, medicated drinking water, medicated dietary supplements, slow-release boluses or other slow-release devices intended to be retained within the gastrointestinal tract. Any of these may incorporate the active ingredients contained within microcapsules or coated with acid-labile or alkali-labile or other pharmaceutically acceptable enteric coatings. Feed premixes or concentrates containing compounds of the present invention for use in preparation of medicated diets, drinking water or other materials for consumption by animals may also be used.

For oral administration, generally the arylpyrazole of formula (I) is administered to an animal at a rate of from 0.1 to 100 mg/kg, preferably from 0.5 to 50 mg/kg and most preferably from 1 to 30 mg/kg.

The present invention also relates to a use of a 1-arylpyrazole of formula (I) as hereinbefore defined to manufacture a composition for the control of parasites, particularly fleas, in or on an animal.

The present invention also relates to a method of cleaning animals in good health comprising the application to the animal of a 1-arylpyrazole of formula (I) or a composition comprising the 1-arylpyrazole to the animal.

The method of cleaning an animal is not a method of treatment of the animal body per se because:

(a) the animal is in good health and requires no substantial treatment to correct a deficiency of health;

(b) the cleaning of the animal is not intended to be done by veterinary personnel, but by persons interested in the cleaning of the animal; and (c) the purpose of such cleaning is to avoid unpleasant conditions for humans and the environment which humans inhabit so as to not infest the said humans with arthropods carried by the animal.

The present invention also provides the use of a composition comprising the 1-arylpyrazole as described supra as an active veterinary substance.

The arylpyrazole is most advantageously administered by use of compositions known to those skilled in the art.

The following non-limiting examples provide an illustration of the way the invention may be worked.

EXAMPLE 1

Compounds A, B, and C are dissolved in dimethylsulfoxide and diluted in cow blood to give a series of concentrations of Compounds A, B and C. The solutions are placed in tubes which are sealed at one end with PARAFILM® membrane. The PARAFILM® end of the tube is abutted against a cage which contains about 10 cat fleas. Fleas are allowed to feed through the PARAFILM®. The blood solutions are changed daily. Mortality is assessed after three days. Compounds A, B and C are substantially move effective than the prior art compounds.

EXAMPLE 2

Compounds A, B and C are formulated as 60 mg/mL formulations in a 1:1 volume/volume solution of dimethylsulfoxide and corn oil. Using this formulation, mixed breed dogs and cats are treated at a rate of 10 mg of the compound per kg of body weight of the animal treated.

All animals are infested with cat fleas (*Ctenocephalides felis*) 1 day prior to administration of the compound. At 8, 15, 22 and 29 days after treatment, the animals are re-infested with fleas. At 1, 9, 16, and 30 days after treatment, the control of fleas and ticks is determined versus an untreated control dog. Immediately after the determination of efficacy, all arthropods are removed from the animals.

Compounds A, B and C are substantially more active than prior art compounds.

While the invention has been described in terms of various preferred embodiments, the person skilled in the art will appreciate that various modifications, substitutions, omissions and changes can be made without departing from the spirit thereof. Accordingly, it is intended that the scope of the present invention be limited solely by the scope of the following claims, including equivalents thereof.

What is claimed is:

1. A method of controlling fleas on an animal in need of such control, said method comprising orally administering to said animal a composition comprising the compound 5-amino-3-cyano-1-(2,6-dichloro-4-pentafluorosulfenylphenyl)-4-trifluoromethylsulfinylpyrazole, 5-amino-3-cyano-1-(2,6-dichloro-4-pentafluorosulfenylphenyl)-4-trifluoromethylsulfenylpyrazole or 5-amino-3-cyano-1-(2,6-dichloro-4-pentafluorosulfenylphenyl)-4-trifluoromethylsulfonylpyrazole, in an amount effective to control fleas which is from 1.2 to 10 mg per kg of body weight of the animal, and a pharmaceutically acceptable carrier or coating.

2. A method of controlling fleas on a dog or cat in need of such control, said method comprising orally administering to said dog or cat a composition comprising the compound 5-amino-3-cyano-1-(2,6-dichloro-4-pentafluorosulfenylphenyl)-4-trifluoromethylsulfinylpyrazole, 5-amino-3-cyano-1-(2,6-dichloro-4-pentafluorosulfenylphenyl)-4-trifluoromethylsulfenylpyrazole or 5-amino-3-cyano-1-(2,6-dichloro-4-pentafluorosulfenylphenyl)-4-trifluoromethylsulfonylpyrazole, in an amount effective to control fleas which is from 1.2 to 10 mg per kg of body weight of the dog or cat, and a pharmaceutically acceptable carrier or coating.

3. A method of controlling fleas on an animal in need of such control, said method comprising orally administering to said animal a composition comprising the compound 5-amino-3-cyano-1-(2,6-dichloro-4-pentafluorosulfenylphenyl)-4-trifluoromethylsulfinylpyrazole, in an amount effective to control fleas which is from 1.2 to 10 mg per kg of body weight of the animal, and a pharmaceutically acceptable carrier or coating.

4. A method of controlling fleas on a dog or cat in need of such control, said method comprising orally administering to said dog or cat a composition comprising the compound 5-amino-3-cyano-1-(2,6-dichloro-4-pentafluorosulfenylphenyl)-4-trifluoromethylsulfinylpyrazole, in an amount effective to control fleas which is from 1.2 to 10 mg per kg of body weight of the dog or cat, and a pharmaceutically acceptable carrier or coating.

* * * * *